Figure 1:
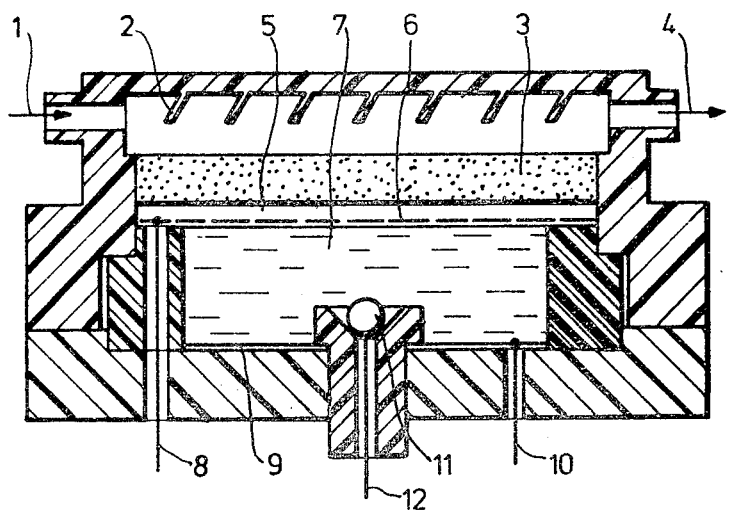

United States Patent [19]

Petersen et al.

[11] 4,235,689
[45] Nov. 25, 1980

[54] APPARATUS FOR DETECTING TRACES OF A GAS

[75] Inventors: Otto Petersen; Hans-Dieter Schmidt, both of Krefeld, Fed. Rep. of Germany

[73] Assignee: Bayer Aktiengesellschaft, Leverkusen, Fed. Rep. of Germany

[21] Appl. No.: 20,120

[22] Filed: Mar. 13, 1979

[30] Foreign Application Priority Data

Mar. 22, 1978 [DE] Fed. Rep. of Germany ....... 2812613

[51] Int. Cl.³ ............................................. G01N 27/54
[52] U.S. Cl. ................................ 204/195 R; 204/1 T
[58] Field of Search .............. 204/195 R, 1 N; 324/29

[56] References Cited

U.S. PATENT DOCUMENTS

| | | | |
|---|---|---|---|
| 3,909,204 | 9/1975 | Allen | 204/195 R X |
| 4,001,103 | 1/1977 | Blurton et al. | 204/195 R |
| 4,052,268 | 10/1977 | Blurton et al. | 204/1 T |
| 4,149,948 | 4/1979 | Petersen et al. | 204/195 R |

FOREIGN PATENT DOCUMENTS 2627271 12/1977 Fed. Rep. of Germany .

*Primary Examiner*—G. L. Kaplan
*Attorney, Agent, or Firm*—Sprung, Felfe, Horn, Lynch & Kramer

[57] ABSTRACT

The measuring cell for detecting traces of nitrogen dioxide comprises a working electrode, preferably a silver mesh coated with silver iodide, an auxiliary and a reference electrode. The working electrode is an ion-selective electrode and cathodically polarized. If a reactor is preceded, in which the gas is oxidized by heating, other nitrogen containing gaseous substances, f. e. acrylonitrile and hydrocyanic acid, can also be detected very sensitively.

6 Claims, 4 Drawing Figures

APPARATUS FOR DETECTING TRACES OF A GAS

The invention relates to an apparatus for detecting traces of nitrogen dioxide in a gaseous mixture, comprising an electro-chemical cell with a working electrode, reference electrode and auxiliary electrode in an organic electrolyte, the working electrode being a polarisable, ion-selective electrode, and also of a power source of constant voltage (potentiostat) and a current measuring device.

Electro-chemical cells for detecting a gas in a gaseous mixture are particularly important in the field of environmental protection. By using them, it is possible to determine if dangerous gases are present in the air. In particular, they should indicate when predetermined concentrations are exceeded, and they therefore have to be sensitive without requiring servicing and operate in a uniform manner for a relatively long period.

An electro-chemical cell having a polarographic device with an ion-selective electrode as working electrode is described in German Offenlegungsschrift No. 26 27 271. It has now been found that traces of nitrogen dioxide in a gaseous mixture can be measured in an apparatus of this type if the working electrode is a silver electrode cathodically polarised and coated with silver iodide and the auxiliary electrode comprises silver. It has also been found that, using an apparatus of this type, other nitrogen containing gaseous substances can also be detected very sensitively if the cell is preceded by a reactor in which the gas is oxidised by heating and conveyed to the working electrode of the test cell after cooling. The invention relates to gas detectors for nitrogen dioxide, acrylonitrile and hydrocyanic acid. According to another embodiment of the invention, acrylonitrile can be measured selectively in addition to hydrocyanic acid.

The working electrode is an ion-selective electrode, for example a silver wire gauze which is coated with silver iodide, and it is polarised as the cathode. The auxiliary electrode consists of silver and an Ag/AgI electrode is advantageously used as the reference electrode. The dependence on temperature is greatly reduced by this symmetrical arrangement about the working electrode.

The electrodes are operated in a potentiostat circuit. The electrolyte is a thickened organic electrolyte. It comprises from 40 to 60% diethyl phthalate, from 25 to 35% propylene carbonate and from 15 to 20% PVC. It also contains means for increasing the conductivity and for stabilising the pH-value.

If nitrogen dioxide is present, iodine is separated at the cathode, but without external current supply in accordance with:

AgI + 2NO$_2$ → AgNO$_3$ + NO + I

As a result of the polarographic process, i.e. the cathodic process

I + e → I' and the anodic process at the auxiliary electrode

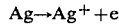

Ag → Ag$^+$ + e retrogradation of silver iodide takes place, i.e. the working electrode is not attacked, but instead, the auxiliary electrode acts as a sacrificial electrode. This exchange of electrons occurs at an operating voltage of about −140 mV (based on the standard hydrogen electrode).

The apparatus according to the invention is illustrated by way of example in the drawings and is described in more detail below.

Figure 2:
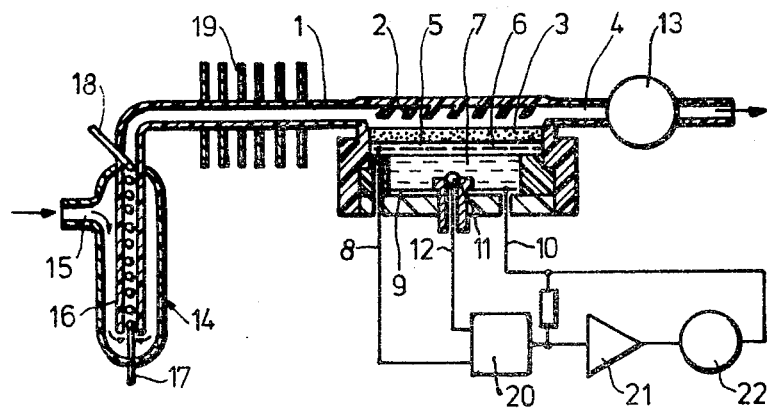
Figure 3:
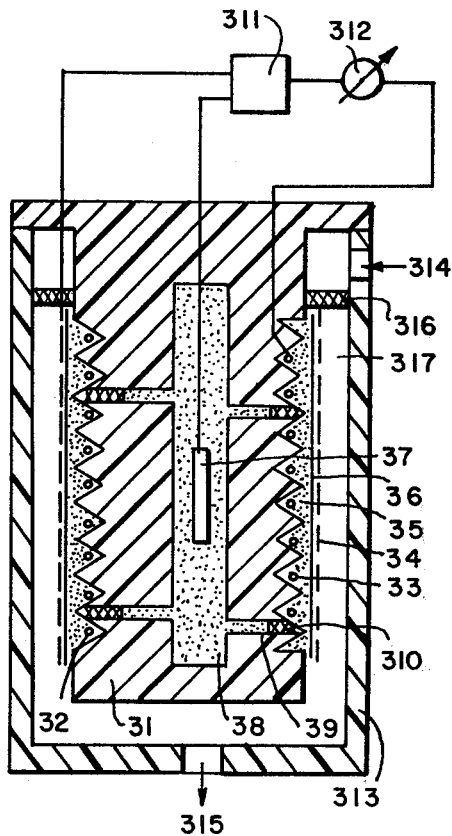
Figure 4:
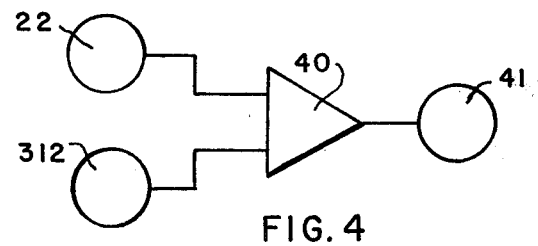

FIG. 1 shows a section through a test cell;
FIG. 2 shows a test cell with a reactor.
FIG. 3 shows a prior art electrochemical cell.
FIG. 4 shows an apparatus using two electrochemical cells in order to sense acrylonitrile in the presence of hydrocyanic acid.

According to FIG. 1, the gaseous mixture to be examined for nitrogen dioxide enters the test cell at 1. The gas-mixture is compelled to completely fill up above the frit 3 by means of spiral guiding fins 2. The gas flows out at 4.

Gas diffuses into the chamber 5 via the frit 3. This chamber is about 1 mm deep, and the base is covered with a working electrode 6 which, in turn, makes close contact with the electrolyte 7.

The working electrode 6 is gauze-like and can be connected to a power source of constant voltage (potentiostat) via 8. The electrolyte 7 is consolidated in a gel form. The auxiliary electrode 9 is composed of silver and is connected to the potentiostat via 10. The reference electrode 11 is composed of silver iodide and connection is made with it via 12.

FIG. 2 shows the complete measuring arrangement with a reactor. Reference numerals 1 to 12 have the same meaning as in FIG. 1. A pump 13 (capacity about 20 l/h) sucks the test gas firstly through a micro-reactor 14. It contains a pre-heater 15 and a heating member 16 which is coated with catalyst. The catalyst is, for example, pyrolusite, and the acrylonitrile is decomposed to carbon dioxide, water and nitrogen dioxide at from 400° to 450° C. The heating member 16, a platinum wire, can be heated via the connections 17 and 18. The gaseous mixture is cooled in the cooler 19 and is guided via 1 into the test cell. 20 is a potentiostat, 21 a post-amplifier, 22 a display and recording instrument.

2 ppm nitrogen dioxide product a primary current of about $2.10^{-6}$ A. The response sensitivity lies below 0.2 ppm; the response time amounts to less than 5 seconds; the zero constant lies at ±3%; the 50% time (time until 50% of the final value is attained) amounts to less than 1 minute.

The electrochemical cell disclosed in U.S. patent application Ser. No. 804,699 filed June 8, 1977 and now abandoned in favor of application Ser. No. 11,343 filed Feb. 12, 1979, corresponding to German application No. 2,627,271, is shown in FIG. 3 and is described hereinafter.

The auxiliary electrode 33 lies at the base of the screw thread 32 cut into the surface of a cylindrical body of polypropylene 31. A mesh wrapped round the threaded part of the cylinder 31 forms the working electrode 34. The electrolyte 35 between the auxiliary electrode 33 and the working electrode 34 is thickened. A foil 36 which is permeable to the electrolytes is advantageously arranged on the internal surface of the working electrode 34 to stabilise the electrolyte mechanically and to reduce the effective quantity of electrolyte, which is advantageous for the time factor. The reference electrode 37 is arranged centrally and dips into an electrolyte 38 which has the same composition as electrolyte 35 but without the thickener. The electrolyte 38 round the reference electrode 37 is electrically coupled to the thickened electrolyte 35 between the auxiliary electrode 33 through channels 39. A diaphragm 310 is installed in each channel 39. This prevents electrolyte 38 from flowing out but fresh electrolyte can be supplied through the diaphragm 310 so that the outer electrolyte 35, which is thickened, maintains its composition for a long time. The voltage of the polarographic stage of the gas which is to be detected is preselected on the potentiostat 311. The instrument 312 indicates a current proportional to the concentration. The polypropylene body 31 is surrounded by a polypropylene housing 313 having a gas inlet 314 and gas outlet 315. An annular frit 316 retains the gas to be measured and provides for a uniform flow of gas through the chamber 317.

In order to measure the presence of acrylonitrile with the simultaneous presence of hydrocyanic acid, the detection of FIG. 2 is used to detect acrylonitrile and the FIG. 3 cell is used to detect hydrocyanic acid, wherein the working electrode is silver/silver iodide. FIG. 4 shows that the difference is the current measurements is obtained in differential amplifier 40 and displayed in current display device 41, thus indicating the concentration of acrylonitrile.

What we claim is:

1. An apparatus for detecting traces of gas in a gaseous mixture, comprising: an electro-chemical cell having a polarizable ion selective working electrode composed of silver coated with silver iodide, a reference electrode and auxiliary electrode composed of silver in an organic electrolyte; means for maintaining a constant voltage between the working electrode and the reference electrode to cathodically polarize the working electrode; a current measuring instrument for measuring the current to the auxiliary electrode; a reactor having a catalyst filling and connected upstream of the electro-chemical cell; cooling means between the reactor and the cell; and means for guiding the gaseous stream to be measured such that the gas is heated in the reactor and catalytically oxidised and is thereafter cooled in the cooling means before it impinges upon the working electrode.

2. A gas detector according to claim 1 for detecting acrylonitrile.

3. An apparatus as claimed in claim 1, wherein the electrolyte consists of from 40 to 60% diethyl phthalate, from 25 to 35% propylene carbonate, and from 15 to 20% polyvinyl chloride.

4. A gas detector according to claims 1 or 2 for detecting nitrogen dioxide.

5. A gas detector according to claims 1 or 2 for detecting hydrocyanic acid.

6. A gas detector for detecting acrylonitrile with the simultaneous presence of hydrocyanic acid comprising: a gas detector for detecting acrylonitrile comprising a first electro-chemical cell having a polarizable ion selective working electrode composed of silver coated with silver iodide, a reference electrode and auxiliary electrode composed of silver in an organic electrolyte, means for maintaining a constant voltage between the working electrode and the reference electrode to cathodically polarize the working electrode and a current measuring instrument for measuring the current to the auxiliary electrode, a reactor having a catalyst filling and connected upstream of the electro-chemical cell, cooling means between the reactor and the cell and means for guiding the gaseous stream to be measured such that the acrylonitrile is heated in the reactor and catalytically oxidised and is thereafter cooled in the cooling means before it impinges upon the working electrode; a second electro-chemical cell for the detection of hydrocyanic acid comprising an ion selective working electrode of silver/silver iodide, an auxiliary electrode, means for maintaining a constant voltage on the working electrode to polarize same at the characteristic voltage for hydrocyanic acid, means for conducting the gas mixture to the boundary between the working electrode and the electrolyte and a current measuring instrument for measuring the current to the auxiliary electrode; and means for measuring the difference between the currents measured in the two cells.

* * * * *